United States Patent [19]

Barth et al.

[11] 3,932,606

[45] Jan. 13, 1976

[54] DENTIFRICE

[75] Inventors: Jordan B. Barth, East Brunswick; Christopher H. Costello, Millington, both of N.J.

[73] Assignee: Colgate-Palmolive Company, New York, N.Y.

[22] Filed: Feb. 7, 1974

[21] Appl. No.: 440,399

[52] U.S. Cl. ............................... 424/52; 424/49
[51] Int. Cl.$^2$ ..................... A61K 7/16; A61K 7/18
[58] Field of Search ........................ 424/49–58; 260/243 R

[56] References Cited
UNITED STATES PATENTS 3,689,485  9/1972  Clauss et al. ............... 260/243 R
3,689,486  9/1972  Clauss et al. ............... 260/243 R

*Primary Examiner*—Shep K. Rose
*Attorney, Agent, or Firm*—Steven J. Baron; Murray M. Grill; Herbert S. Sylvester

[57] ABSTRACT

There is disclosed a dentifrice containing as sweetener approximately by weight 0.01 to 10.0% of an alkali or alkaline earth metal salt or free base of 3,4-dihydro-1,2,3-oxathiazin-4-one, as well as dental creams, mouth rinses and chewable tablets derived therefrom.

23 Claims, No Drawings

DENTIFRICE

This invention relates to a novel dentifrice preparation, more particularly, to a dentifrice having therein a new stable sweetener. It has repeatedly been stated that taste and flavor are perhaps the most important single aspect with respect to the consumer acceptance of a dentifrice formulation. The selection of acceptable sweetener and flavoring ingredients is therefor of paramount importance in the formulation of the dentifrice. It has oftentimes been stated that the foregoing is both an art as well as a science. It is an art in the sence that it requires the blending of the various components with the sweetening agents such that the final composition contains a pleasing taste as well as in providing for a composition in which the sweetener is stable. It is the foregoing that has presented particular difficulties in incorporating sweetening agents in a dentifrice inasmuch as the former must be compatible with the latter and remain essentially unchanged over the shelf life of the product.

At the present time, there are a relatively few sweeteners which are both currently available for use in dentifrice as well as generally acceptable for use therein. One of the better known sweeteners is saccharine, however, its use may present some difficulties and oftentimes, when used as the sole sweetener, leaves a bitter taste. Other more exotic sweeteners though available, are generally not acceptable for use in the dentifrices due to their stability problems vis-a-vis the various components in the dentifrice. Some of those sweeteners which do not have stability problems have the drawback that they are not suitable for use as a primary sweetener due to the unacceptable timelag prior to the on set of their sweetness and/or their associated side tastes. Inasmuch as dentifrices generally contain a detergent like material, the sweetener employed therein must have the quality of a rapid onset of sweetness so as to mask the generally bitter flavor associated with detergent-like ingredients. The use of low intensity sweeteners is, therefore, not practical for use in most dentifrice formulations. Merely increasing the amount of low intensity sweetener so as to overcome the foregoing deficiencies does not prove very helpful inasmuch as a dentifrice generally contains large amounts of humectants, polishing agents, water and the like and therefore from a volume point of view, it is not practical.

A further consideration in formulating a dentifrice relates to the fact that the polishing agents employed therein are generally absorbent materials and therefore there may be a selective absorption onto the polishing agent of the sweetener with accompanying change in physical form of the toothpaste, chemical changes and resultant overall flavor.

It is accordingly an object of this invention to provide for a novel dentifrice containing a new sweetening agent, which sweetening agent is operative to function as a prime sweetener therein.

It is another object of the invention to avoid one or more drawbacks of the prior art.

Broadly speaking, the invention includes the provision of a dentifrice containing approximately by weight 0.01 to 10.0% of an alkali or alkaline earth metal salts or free base of 3,4-dihydro-1,2,3-oxathiazin-4-one, particularly, the potassium, calcium and sodium salts thereof.

The precursor material from which the metal salt is derived is prepared by reacting a ketone of the general formula $R_1$—$CH_2$—$CO$—$R_2$ wherein R represents an alkyl radical with 1 to 10 carbon atoms or an aromatic hydrocarbon radical with up to 10 carbon atoms and $R_2$ represents an alkyl group with 1 to 11 carbon atoms or an aromatic hydrocarbon radical with up to 10 carbon atoms, $R_1$ and $R_2$ may be straight or branched chain. $R_1$ and $R_2$ can be bonded to an isocyclic radical or to a ring substituted by additional hydrocarbon radicals, wherein $R_1$ and $R_2$ together contain a maximum of 14 carbon atoms; said ketone is thereafter reacted with a fluorosulphonyl isocyanate, the resulting keto carboxyl amide -N-fluoride is thereafter treated with an alkali base at a pH of about 5 to 12 to form the oxathiazin salt which is thereafter isolated. Various other methods for the preparation of the foregoing salt may also be employed such as those taught in German Pat. No. P 2 001 017.7 printed on July 22, 1971. The free base may be easily prepared therefrom in accordance with procedures known in the art.

The salt or base referred to above may be admixed with the components of the dentifrice in any suitable order. Ordinarily, the amount of the sweetener may vary from about 0.01 to about 10.0%, by weight, preferably about 0.01 to about 5% based upon the total weight of the dentifrice.

The sweetener may be admixed with another sweetener if desired, though the latter is not necessary. An example of the foregoing might be the combination with saccharine, such as for example, to reduce the bitter taste associated with the latter. The sweetener may also be admixed with suitable flavoring oils where desired, in accordance with known procedures. The sweetener is generally incorporated with the dentifrice at room temperature, though temperatures of 140° to 160°F or higher are permissible.

The dentifrice formulation of the invention includes liquids and solids that are proportioned to form a creamymass of desired consistency which is extrudable from an aerosol container or a collapsible tube (for example aluminum or lead). In general, the liquids in the dental cream will comprise chiefly water, glycerine, aqueous solutions of sorbitol, propylene glycol, polyethylene glycol 400, etc., including suitable mixtures thereof. It is advantageous usually to use a mixture of both water and a humectant or binder such as glycerine or sorbitol. The total liquid content will generally be about 20 to 75 percent by weight of the formulation. It is preferred to use also a gelling agent in dental creams and gels such as the natural and synthetic gums and gum-like materials, for example, Irish moss, gum tragacanth, methyl cellulose, polyvinylpyrrolidone, hydrophilic colloidal carboxyvinyl polymers, such as those sold under the trademark Carbopol 934 and 940 and synthetic silicated clays such as those sold under the trademark Laponite CP and Laponite SP. These grades of Laponite have the formula

The solid portion of the vehicle is usually present in an amount of up to about 10 percent preferably about 0.2 to 5 percent by weight of the formulation.

In the preparation of tooth powders, it is usually sufficient to admix mechanically, e.g., by milling, the various solid ingredients, in appropriate quantities and particle sizes.

In chewable dental tablets the solids and liquids are proportioned similarly to the amounts in dental creams and the flavor is blended with the solids and liquids, a waxy matrix such as polyethylene glycol having a molecular weight of about 6,000 by weight, generally in amount of about 4–20 percent by weight, in order to facilitate a tablet of desired size and shape.

In other oral preparations, such as mouthwashes and the like, the carrier is an aqueous vehicle which may comprise about 20–99 percent by weight of the preparation. Typically, the vehicle also includes about 5–30 percent by weight of a nontoxic alcohol, such as ethanol. Preferred mouthwashes generally will comprise approximately by weight (a) 65 to 85% water, (b) 5 to 25% non-toxic alcohol and (c) 0.5 to 3% surface-active agent; more preferably about 68 to 78% water and up to about 15% of at least one material selected from the group consisting of glycerine, sorbitol and propylene glycol and wherein said alcohol is denatured ethanol. Optimally, there will be present about 10 to 20% ethanol, 8 to 12% glycerine and about 0.01 to 1.0% of said salt or free base.

The dental cream formulations will generally also include a dentally acceptable, substantially water insoluble, polishing agent of the type commonly employed in dental creams. Representative polishing agents include, for example, dicalcium phosphate, tricalcium phosphate, insoluble sodium metaphosphate, aluminum hydroxide, including hydrated alumina, colloidal silica, magnesium carbonate, calcium carbonate, calcium pyrophosphate, bentonite, etc., including suitable mixtures thereof. When employed, it is preferred to use the water insoluble phosphate salts as the polishing agent and more particularly insoluble sodium metaphosphate and/or a calcium phosphate such as dicalcium phosphate dihydrate in dental creams. When visually clear gels are employed, a polishing agent of colloidal silica, such as those sold under the trademark Syloid as Syloid 72 and Syloid 74 or under the trademark Santocel as Santocel 100 and synthetic alkali metal aluminosilicate complexes may be particularly useful, since they have refractive indices close to the refractive indices of gelling agent-liquid (generally including humectants such as glycerine and sorbitol) systems commonly used in dentifrices. When employed, the total polishing agent content is generally in amounts from about 15 to 75 percent by weight in a dental cream. In a visually clear gel the total amount of polishing agent is generally from about 5 to 50 percent by weight.

Organic surface-active agents are used in the compositions of the present invention to assist in achieving thorough and complete dispersion of the instant compositions throughout the oral cavity and render the instant compositions more cosmetically acceptable. The organic surface-active material may be anionic, nonionic, ampholytic, or cationic in nature, and it is preferred to employ as the surface-active agent a detersive material which imparts to the composition detersive and foaming properties. Suitable such detergents are water-soluble salts of higher fatty acid monoglyceride monosulfates, such as the sodium salt of the monosulfated monoglyceride of hydrogenated coconut oil fatty acids, higher alkyl sulfates, such as sodium lauryl sulfate, alkyl aryl sulfonates, such as sodium dodecyl benzene sulfonate, higher alkyl sulfoacetates, higher fatty acid ester of 1,2-dihydroxy propane sulfonates, olefin sulfonates and the substantially saturated higher aliphatic acyl amides of lower aliphatic amino carboxylic acid compounds, such as those having 12 to 16 carbon atoms in the fatty acid, or acyl radicals, and the like. Examples of the last mentioned amides are N-lauroyl sarcosine, and the sodium, potassium and ethanolamine salts of N-lauroyl, N-myristoyl, or N-palmitoyl sarcosine which should be substantially free from soap or similar higher fatty acid material which tends to substantially reduce the effect of these compounds. The use of these sarcosinate compounds in the dentifrice compositions of the present invention is particularly advantageous since these materials exhibit a prolonged and marked effect in the inhibition of acid formation in the oral cavity due to carbohydrate breakdown in addition to exerting some reduction in the solubility of tooth enamel in acid solutions.

Other particularly suitable surface active materials include nonionic agents such as condensates of sorbitan monostearate with approximately 60 moles of ethylene oxide, condensates of ethylene oxide with propylene oxide, condensates of propylene glycol ("Pluronics"), and amphoteric agents such as quaternized imidazole derivatives which are available under the trademark "Miranol" such as Miranol $C_2M$.

Other suitable nonionic detergents are the condensation products of an $\alpha$-olefin oxide containing 10 and 20 carbon atoms, a polyhydric alcohol containing 2 to 10 carbons and 2 to 6 hydroxyl groups and either ethylene oxide or a heteric mixture of ethylene oxide and propylene oxide. The resultant detergents are heteric polymers having a molecular weight in the range of 400 to about 1600 and containing 40% to 80% by weight of ethylene oxide, with an $\alpha$-olefin oxide to polyhydric alcohol mole ratio in the range of about 1:1 to 1:3. These detergents are manufactured using well-known polymerization techniques under conditions of high temperature and high pressure. The olefin oxide and polyhydric alcohol usually are added to the reactor prior to the addition of ethylene oxide. These nonionic detergents may be mixed with similar nonionic detergents as well as other type nonionic detergents described herein.

It is preferred to use from about 0.05 to 5% by weight of the foregoing surface-active materials in the instant oral preparations.

Various other materials may be incorporated in the dentifrice formulations of this invention. Examples thereof are coloring or whitening agents or dyestuffs, preservatives, silicones, chlorophyll compounds, ammoniated materials such as urea, diammonium phosphate and mixtures thereof, and other constituents. These adjuvants are incorporated in the instant compositions in amounts which do not substantially adversely affect the properties and characteristics desired and are selected and used in proper amount depending upon the particular type of preparation involved.

The compositions of the present invention may also contain a fluorine-containing compound having a beneficial effect on the care and hygiene of the oral cavity, e.g., diminution of enamel solubility in acid and protection of the teeth against decay. Examples thereof include sodium fluoride, stannous fluoride, potassium fluoride, potassium stannous fluoride ($SnF_2KF$), potassium fluorozirconate, sodium hexafluorostannate, stannous chlorofluoride, and sodium monofluorophosphate. These materials which dissociate or release fluorine-containing ions, suitably may be present in an effective but non-toxic amount usually within the range of about 0.1 to 1% by weight, based on the water soluble fluorine content thereof. Sodium fluoride, stannous fluoride, and sodium monofluorophosphate are particularly preferred, as well as mixtures thereof.

Antibacterial agents may also be employed in the oral preparation of the instant invention to provide a total content of such agents of up to about 5% by weight, preferably 0.01 to 5.0%, most preferably about 0.05 to 1.0%. Typical antibacterial agents include:

- $N^1$-(4-chlorobenzyl)-$N^5$-(2,4-dichlorobenzyl) biguanide;
- p-chlorophenyl biguanide;
- 4-chlorobenzhydryl biguanide;
- 4-chlorobenzhydrylguanylurea;
- N-3-lauroxpropyl-$N^5$-p-chlorobenzylbiguanide;
- 1-(lauryldimethylammonium)-8-(p-chlorobenzyldimethylammonium) octane dichloride;
- 5,6-dichloro-2-guanidinobenzimidazole;
- $N^1$-p-chlorophenyl-$N^5$-laurylbiguanide;
- 1,6-di-p-chlorophenyl biguanidohexane;
- 1,6-bis(2-ethylhexyl biguanido) hexane;
- 5-amino-1,3-bis(2-ethylhexyl)-5-methylhexahydropyrimidine;

and their non toxic acid addition salts.

Synthetic finely divided pyrogenic silica such as those sold under the trademark Cab-O-Sil M-5, Syloid 244, Syloid 266 and Aerosil D-200 may also be employed in amounts of about 1–5% by weight to promote thickening or gelling and to improve clarity of the dentifrice.

The taste of the new compositions may be modified by employing suitable flavoring or sweetening materials. Examples of suitable flavoring constituents include the flavoring oils, e.g., oil of spearmint, peppermint, wintergreen, sassafras, clove, sage, eucalyptus, marjoram, cinnamon, lemon and orange as well as sodium methylsalicylate. Suitable additional sweetening agents include sucrose, lactose, maltose, sorbitol, sodium cyclamate and perillartine as well as saccharine where desired. Suitably, flavor and sweetening agents may together comprise from about 0.01 to 5% or more of the compositions of the instant invention. Additionally, the new dental formulations can be provided with the unusual biting flavor of chloroform. Accordingly, instead of or in addition to the foregoing flavoring or additional sweetening materials, the new formulation can include up to about 5%, preferably between .1 and 5%, by weight of chloroform and chloroform flavoring.

It is desirable to adjust the pH of the dental cream formulations to the range of about 3 to 10 using such acids as citric, acetic, chloropropionic, malonic, formic, fumaric, methoxyacetic, and propionic of salts thereof. Lower pH's than 3 are generally undesirable for oral use. When stannous ions are present, the pH is preferably lower than about 5. The preferred pH range is 3.5 to about 5.0 when stannous ions are present and about 4.5 to about 7.0 in the absence of stannous ion.

The following specific examples are further illustrative of the nature of the present invention but it is understood that the invention is not limited thereto. Dental cream formulations are prepared in the usual manner, except as indicated, and all amounts and proportions are by weight except as otherwise indicated.

EXAMPLE 1 - DENTAL CREAM

| | % |
|---|---|
| Glycerine | 9.474 |
| Sorbitol | 17.000 |
| Carboxymethylcellulose (Na salt) | 1.100 |
| Na Benzoate | 0.500 |
| Potassium 3,4-dihydro- | |
| 1,2,3-oxathiazin-4-one | 0.600 |
| Water | 18.341 |
| $Na_2PO_3F$ | 0.760 |
| $TiO_2$ | 0.400 |
| Insoluble Na Metaphosphate | 41.850 |
| Anhydrous dicalcium phosphate | 5.000 |
| Alumina - Hydrated | 1.000 |
| 35% Solution of Sodium N-lauroyl sarcosinate | 2.000 |
| Na Lauryl sulfate | 0.975 |
| Flavor | 1.000 |
| | 100.00 |

EXAMPLE 2 - DENTAL CREAM

| | Parts |
|---|---|
| Antimicrobial agent | 0.1 |
| Sodium benzoate | 0.15 |
| Calcium 3,4-dihydro-1,2,3-oxathiazin-4-one | 0.20 |
| Sodium lauryl sulfate | 1.5 |
| Insoluble sodium metaphosphate | 40.6 |
| Dicalcium phosphate dihydrate | 5.0 |
| Titanium dioxide | 0.4 |
| Stannous fluoride | 0.4 |
| Gum tragacanth | 1.4 |
| Oil of wintergreen | 1.0 |
| Color | 0.03 |
| Water | 22.12 |
| Glycerine (99.3%) | 27.10 |

This composition is used by brushing the teeth therewith at least once daily.

In the above dental cream, the sodium lauryl sulfate may be replaced by sodium-N-lauroylsarcosinate, and the free base of the antimicrobial agent may be replaced by the hydrochloride salt thereof.

EXAMPLE 3 - DENTAL CREAM

| | Parts |
|---|---|
| Antimicrobial agent | 0.1 |
| Sodium 3,4-dihydro-1,2,3-oxathiazin-4-one | 0.2 |
| Sodium benzoate | 0.5 |
| Tetrasodium pyrophosphate | 0.25 |
| Dicalcium phosphate dihydrate | 36.75 |
| Calcium carbonate | 5.0 |
| Sodium carboxymethylcellulose | 0.75 |
| Olefin sulfonate ($C_{14-16}$ olefin-Na salt) | 2.0 |
| Glycerine (99.3%) | 23.95 |
| Oils of peppermint and spearmint, 1:1 | 0.8 |
| Water | 19.7 |

EXAMPLE 4 - TRANSPARENT CREAM

| | Parts |
|---|---|
| Glycerine | 25.00 |
| Sodium carboxymethylcellulose | 0.70 |
| Calcium 3,4-dihydro-1,2,3 oxathiazin-4-one | 0.17 |
| Sodium benzoate | 0.50 |
| Sorbitol (70%) | 44.83 |
| Water | 3.00 |
| Sodium aluminum silicate | 16.00 |
| Syloid 244 | 5.00 |
| Flavor | 1.00 |
| Sodium lauryl sulfate | 2.00 |

EXAMPLE 5 - CHLOROFORM CONTAINING CREAM

| Components | Parts |
|---|---|
| Glycerine | 22.00 |
| Carboxymethyl cellulose (Na salt) | 0.80 |
| Tetrasodium pyrophosphate | 0.25 |
| Sodium benzoate | 0.50 |
| Na-3,4-dihydro 1,2,3-oxathiazin-4-one | 0.50 |
| $H_2O$ | 20.95 |
| Dicalcium phosphate.$_2H_2O$ | 46.00 |
| Calcium carbonate | 5.00 |
| Flavor oil | 1.00 |
| Chloroform | 1.00 |
| Na Lauryl sulfate | 2.00 |
| | 100.00 |

EXAMPLE 6 - CLEAR CREAM

The following visually clear dental cream is prepared:

| Components: | Parts |
|---|---|
| Sorbitol (70%) | 75.0 |
| Glycerine | 25.0 |
| Laponite SP | 2.0 |
| Sodium N-lauroyl sarcosinate | 2.0 |
| Calcium 3,4-dihydro-1,2,3-oxathiazin-4-one | 0.1 |
| Aerosil D200 | 3.0 |
| Sodium aluminumsilicate | 16.0 |
| Flavor | 1.0 |
| Color | 1.0 |
| Water | 20.0 |

The sodium aluminumsilicate employed is a complex having a refractive index of 1.46, a moisture content of about 6 percent, an average particulate size of about 35 microns and a sieve loose bulk density of about 0.07 g./cc.

EXAMPLE 7 - MOUTH RINSE

| | Parts |
|---|---|
| Antimicrobial agent | 0.1 |
| Sorbitan monostearate polyoxyethylene condensate containing about 60 moles of ethylene oxide | 0.6 |
| Potassium 3,4-dihydro-1,2,3-oxathiazin-4-one | 0.035 |
| Alcohol | 14.78 |
| Water | 83.87 |
| Color | 0.04 |
| Oil of lemon | 0.50 |

This composition is used by rinsing of the oral cavity with about 10 cc. thereof once or more often daily.

EXAMPLE 8 - CHEWABLE TABLET FOR BRUSHING

| | Parts |
|---|---|
| Insoluble sodium metaphosphate | 32.59 |
| Dicalcium phosphate dihydrate | 4.03 |
| Poly(ethylene glycol) having a molecular weight of about 6000 | 5.00 |
| Calcium 3,4-dihydro-1,2,3-oxathiazin-4-one | 0.25 |
| Sodium carboxymethylcellulose | 1.25 |
| Sodium lauryl sulfate | 2.25 |
| Starch | 3.0 |
| Mannitol | 47.3 |
| Talc | 0.5 |
| Magnesium stearate | 1.25 |
| Flavor, color, etc. | 2.48 |
| Antimicrobial agent | 0.1 |

The tablet is employed as a dentifrice by introducing into the mouth a tablet thereof having a weight of about 0.5 grams, crushing it between the teeth, and then brushing the teeth in the usual fashion with saliva acting as a fluid vehicle, for the brushed tablet particles.

Although the foregoing specific examples include preferred and typical formulations, they should not be taken as limitations on the invention. Accordingly, reference should be made to the following claims in determining the full scope of the invention.

We claim:

1. A dentifrice having a vehicle with a pH of about 3 to about 10 and including a surface active agent with an otherwise potentially bitter taste and containing as sole or prime high intensity bitter taste masking sweetener approximately by weight 0.01 to 10.0% of a member selected from the group consisting of 3,4-dihydro-1,2,3-oxathiazin-4-one, the alkali metal salts and the alkaline earth metal salts thereof.

2. A dentifrice as defined in claim 1 wherein said salt is the potassium or calcium salt.

3. A dentifrice as defined in claim 1 additionally containing 0.1 to 12.0% of a member selected from the group consisting of flavoring oils, sweetening agents and mixtures thereof, one of which may otherwise have a potentially bitter after taste.

4. A dentifrice as defined in claim 1 further containing an aqueous vehicle for said member.

5. The composition of claim 4 wherein said aqueous vehicle contains about 5 to 30% of a non-toxic alcohol.

6. A dentifrice as defined in claim 3 wherein said vehicle includes a water-insoluble dental polishing agent.

7. A dentifrice as defined in claim 1 further containing a fluorine compound having a beneficial effect on the care and hygiene of the oral cavity in an effective but non-toxic amount.

8. A dentifrice as defined in claim 7 wherein said fluorine containing compound is selected from the group consisting of sodium fluoride, stannous fluoride, potassium fluoride, potassium stannous fluoride, sodium hexafluorostannate, stannous chlorofluoride, sodium fluorozirconate and sodium monofluorophosphate.

9. A dentifrice as defined in claim 1 further containing an effective amount of an anti-bacterial agent.

10. A dentifrice as defined in claim 6 wherein said polishing agent is about 15-95 percent by weight of the vehicle.

11. A dentifrice as defined in claim 1 wherein said surface-active agent is selected from the group consisting of water-soluble sulfates of compounds having long chain alkyl radicals.

12. A dentifrice as defined in claim 1 wherein said surface active agent is an olefin sulfonate.

13. A dentifrice as defined in claim 1 wherein said surface active agent is sodium lauroyl sarcosinate.

14. A dentifrice as defined in claim 1 in the form of a toothpaste.

15. A dentifrice as defined in claim 1 in the form of a tooth powder.

16. A dentifrice as defined in claim 1 in the form of a chewable tablet.

17. An aqueous mouthwash containing as an essential ingredient said salt or free base as defined in claim 1.

18. A mouthwash as defined in claim 17 containing approximately by weight (a) 65 to 85% water, (b) 5 to 25% non-toxic alcohol and (c) 0.5 to 3% surface-active agent.

19. A mouthwash as defined in claim 17 containing about 68 to 78% water and up to about 15% of at least one material selected from the group consisting of glycerine, sorbitol and propylene glycol and wherein said alcohol is denatured ethanol.

20. A mouthwash as defined in claim 19 containing about 10 to 20% ethanol, 8 and 12% glycerine and about 0.01 to 1.0% of said salt.

21. A dentifrice as defined in claim 1 wherein said salts are selected from the group consisting of sodium, potassium and calcium.

22. A dentifrice as defined in claim 21 wherein said salt is potassium.

23. A dentifrice as defined in claim 21 wherein said salt is calcium.

* * * * *